(12) United States Patent
Moulton

(10) Patent No.: US 8,074,338 B2
(45) Date of Patent: Dec. 13, 2011

(54) VASCULAR ACCESS DEVICES INCLUDING A TEAR-RESISTANT SEPTUM

(75) Inventor: William G. Moulton, West Jordan, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 1072 days.

(21) Appl. No.: 11/935,100

(22) Filed: Nov. 5, 2007

(65) Prior Publication Data

US 2008/0108939 A1 May 8, 2008

Related U.S. Application Data

(60) Provisional application No. 60/864,540, filed on Nov. 6, 2006.

(51) Int. Cl.
*B23P 17/00* (2006.01)
*A61M 39/10* (2006.01)

(52) U.S. Cl. ...... 29/527.1; 29/557; 29/558; 29/890.126; 29/890.127; 604/533; 604/256

(58) Field of Classification Search ............... 29/527.1, 29/527.5, 527.6, 890.126, 890.127, 890.128, 29/890.132, 557, 558; 604/533, 256, 288.01
See application file for complete search history.

(56) References Cited

U.S. PATENT DOCUMENTS

| | | | |
|---|---|---|---|
| 4,765,588 A | 8/1988 | Atkinson | |
| 4,809,679 A * | 3/1989 | Shimonaka et al. | 600/154 |
| 5,147,305 A * | 9/1992 | Nakamura et al. | 604/110 |
| 5,215,537 A * | 6/1993 | Lynn et al. | 604/244 |
| 5,251,873 A | 10/1993 | Atkinson et al. | |
| 5,295,657 A | 3/1994 | Atkinson | |
| 5,295,658 A | 3/1994 | Atkinson et al. | |
| 5,342,316 A | 8/1994 | Wallace | |
| 5,441,487 A | 8/1995 | Vedder | |
| 5,474,544 A | 12/1995 | Lynn | |
| 5,501,426 A | 3/1996 | Atkinson et al. | |
| 5,533,708 A | 7/1996 | Atkinson et al. | |
| 5,549,651 A | 8/1996 | Lynn | |
| 5,699,821 A | 12/1997 | Paradis | |
| 5,957,898 A | 9/1999 | Jepson et al. | |
| 6,068,011 A | 5/2000 | Paradis | |
| 6,079,432 A | 6/2000 | Paradis | |
| 6,171,287 B1 | 1/2001 | Lynn et al. | |
| 6,177,037 B1 | 1/2001 | Mayer | |
| 6,261,282 B1 | 7/2001 | Jepson et al. | |
| 6,344,033 B1 | 2/2002 | Jepson et al. | |
| 6,595,964 B2 | 7/2003 | Finley et al. | |
| 6,651,956 B2 | 11/2003 | Miller | |
| 6,669,681 B2 | 12/2003 | Jepson et al. | |
| 6,866,656 B2 | 3/2005 | Tingey et al. | |
| 6,908,459 B2 * | 6/2005 | Harding et al. | 604/533 |
| 7,306,579 B2 * | 12/2007 | Fujii | 604/244 |

(Continued)

FOREIGN PATENT DOCUMENTS
WO     WO 91/05581 A1     5/1991

*Primary Examiner* — Essama Omgba
(74) *Attorney, Agent, or Firm* — Mony R. Ghose; Kirton & McConkie

(57) ABSTRACT

Methods of manufacturing septa for use with vascular access devices include forming a septum body and forming a slit within the septum body.

20 Claims, 10 Drawing Sheets

U.S. PATENT DOCUMENTS

| | | | | |
|---|---|---|---|---|
| 7,713,250 | B2 * | 5/2010 | Harding et al. | 604/256 |
| 7,722,563 | B2 * | 5/2010 | Isaacson et al. | 604/86 |
| 7,785,299 | B2 * | 8/2010 | Crawford et al. | 604/246 |
| 7,806,890 | B2 * | 10/2010 | McKinnon et al. | 604/533 |
| 7,947,032 | B2 * | 5/2011 | Harding et al. | 604/533 |
| 7,997,032 | B2 * | 8/2011 | Riley et al. | 52/24 |
| 7,998,122 | B2 * | 8/2011 | Lynn et al. | 604/256 |
| 2002/0193752 | A1 * | 12/2002 | Lynn | 604/249 |
| 2003/0109853 | A1 * | 6/2003 | Harding et al. | 604/536 |
| 2003/0208165 | A1 * | 11/2003 | Christensen et al. | 604/256 |
| 2004/0199126 | A1 * | 10/2004 | Harding et al. | 604/256 |
| 2005/0256500 | A1 | 11/2005 | Fujii | |
| 2006/0129112 | A1 * | 6/2006 | Lynn | 604/256 |
| 2006/0241759 | A1 | 10/2006 | Trieu | |
| 2007/0225648 | A1 * | 9/2007 | Winsor et al. | 604/167.04 |
| 2008/0108956 | A1 * | 5/2008 | Lynn et al. | 604/256 |
| 2008/0132832 | A1 * | 6/2008 | McKinnon et al. | 604/93.01 |
| 2009/0088729 | A1 * | 4/2009 | Stout | 604/533 |
| 2010/0179489 | A1 * | 7/2010 | Harding et al. | 604/256 |
| 2010/0298782 | A1 * | 11/2010 | Winsor et al. | 604/247 |

* cited by examiner

VASCULAR ACCESS DEVICES INCLUDING A TEAR-RESISTANT SEPTUM

RELATED APPLICATIONS

This application claims the benefit of U.S. Provisional Application No. 60/864,540, filed Nov. 6, 2006, entitled VASCULAR ACCESS DEVICES INCLUDING A TEAR-RESISTANT SEPTUM, which is incorporated herein by reference.

BACKGROUND OF THE INVENTION

The present disclosure relates to infusion therapy with vascular access devices. Infusion therapy is one of the most common health care procedures. Hospitalized, home care, and other patients receive fluids, pharmaceuticals, and blood products via a vascular access device inserted into the vascular system. Infusion therapy may be used to treat an infection, provide anesthesia or analgesia, provide nutritional support, treat cancerous growths, maintain blood pressure and heart rhythm, or many other clinically significant uses.

Infusion therapy is facilitated by a vascular access device. The vascular access device may access a patient's peripheral or central vasculature. The vascular access device may be indwelling for short term (days), moderate term (weeks), or long term (months to years). The vascular access device may be used for continuous infusion therapy or for intermittent therapy.

A common vascular access device is a plastic catheter that is inserted into a patient's vein. The catheter length may vary from a few centimeters for peripheral access to many centimeters for central access. The catheter may be inserted transcutaneously or may be surgically implanted beneath the patient's skin. The catheter, or any other vascular access device attached thereto, may have a single lumen or multiple lumens for infusion of many fluids simultaneously.

Vascular access devices commonly include a Luer adapter, or other connector or adapter, to which other medical devices may be attached. For example, an IV (intravenous) administration set may be attached to a vascular access device to provide a fluid conduit for the continuous infusion of fluids and pharmaceuticals from an intravenous (IV) bag. A variety of medical devices may cooperate with vascular access devices to provide selective, temporary, or long-term access to the vascular system of a patient. A vascular access device may include a body having a lumen through the body and a septum for selectively closing the lumen. The septum may be opened with a blunt cannula, a male Luer of a medical device, or other suitable medical device.

Vascular access devices provide many significant benefits to patients and medical practitioners. A vascular access device is most beneficial to patients when the septum forms a proper seal between the accessed vascular system and the outside or external environment. In an ideal vascular access device, the septum would continuously seal the patient's vascular system, which may include external vascular equipment intentionally coupled to the patient's internal vascular system by a medical practitioner, from the external environment.

As with most systems, one of the biggest challenges to the proper function of the vascular access device is when there is a change in the system, such as when different medical devices are connected or disconnected from the vascular access device. If the seal against the external environment is broken during the connection or disconnection of a medical device, there is the possibility of infection being introduced into the patient's vascular system. Additionally, if a pressure difference is created across the vascular access device, there becomes the possibility that blood will be drawn up the catheter system and possibly into the vascular access device or beyond. Alternatively, a pressure difference across the vascular access device may make it more difficult to couple other medical devices to the vascular access device.

As introduced above, vascular access devices are often coupled with a blunted cannula, such as the tip of a syringe, with a male Luer connector, or with other medical devices. These medical devices may be coupled to the vascular access devices by pressing a portion of the medical device into a slit or passage in the septum. Some medical devices are coupled to the vascular access device through a twisting motion by which the body or other portion of the medical device is coupled to the body of the vascular access device and by which a portion of the medical device is disposed in the slit or passage of the septum. Other methods of coupling the vascular access device to one or more medical devices may be used as well.

Regardless of the methods used to couple medical devices to the vascular access device, repeated transitions of the septum between open and closed configurations applies stress to the septum. In some experiences the septum has been seen to tear, either slightly or more significantly, at the edges of the slit that allows other devices to access the internal vascular system through the lumen of the body. In previous vascular access devices, two common tear patterns have been observed: radial tearing and circumferential tearing. Depending on the nature of the tear, the impacts of the tear may include a decrease in the quality of the seal formed by the septum or pieces or particles of the septum breaking free from the remainder of the septum. In any event, a septum that is modified from the manufacturer's intended and safety-tested design is not preferred for a number of reasons. The present disclosure is directed to vascular access devices, and methods of manufacturing vascular access devices, that include a tear-resistant septum.

BRIEF SUMMARY OF THE INVENTION

A method of manufacturing a vascular access device may include having a first body end region and a second body end region and defining a passage extending through both body end regions, forming and/or preparing a septum, forming and/or preparing a slit, and disposing at least a portion of the septum in the body. The septum may include a first septum end region and a second septum end region. The slit may extend from the first septum end region to the second septum end region of the septum. Disposing at least a portion of the septum in the body may include disposing at least a portion of the septum in the body to at least substantially seal the passage extending through the body. The slit of the septum may be adapted to provide selective passage through the septum and the body. The septum may be configured to resist tearing.

The septum may include a longitudinal axis and/or a top disk. The slit may have a slit width between a slit first end and a slit second end. The slit width may extend orthogonally to the longitudinal axis.

Preparing the slit may include cutting the septum, drilling into the septum, molding the slit within the septum, melting material of the septum, combining at least two initially separate portions of the septum, varying the depth of the slit within the septum, varying the angle of the slit within the septum, molding the septum, influencing the shape of the septum, cutting an arc-shaped slit in the septum, cutting a meandering slit in the septum, cutting the slit across the entire width of the septum, and/or cutting multiple intersecting cuts in the septum.

Cutting an arc-shaped and/or meandering slit may include cutting with a substantially planar blade. Cutting a meandering slit may include cutting a curved and/or pointed meandering slit.

Preparing the septum may include molding a protective material in communication with the septum, drilling into the septum, and/or molding a material in communication with the septum after drilling into the septum. Preparing the slit may include influencing the shape of the septum and later cutting the septum.

The slit may include at least two ends, and molding the septum may include forming polymer chains in the septum that are oriented at an angle greater than zero degrees in relation to the direction of the ends of the slit, forming polymer chains in the septum that are oriented substantially perpendicular to the direction of the ends of the slit, and/or orienting molding gates to encourage the flow of a molding material in a direction that is not parallel with the direction of the ends of the slit.

A method of manufacturing a septum for use with a vascular access device may include forming a septum body, forming a slit within the septum body, and/or discouraging the septum body from tearing. Forming the septum may include strategically directing the flow of the septum material during molding. Forming the slit may include cutting the slit, drilling into the septum, melting material of the septum, molding the slit into the septum, combining at least two initially separate portions of the septum, and/or influencing the shape of the septum.

These and other features and advantages of the present disclosure may be incorporated into vascular access devices and will become more fully apparent from the following description and appended claims, or may be learned by the practice and implementation of the present disclosure. As described above, the present disclosure does not require that all of the features described herein be incorporated into every embodiment nor is it required that certain features be used exclusive of other features. Vascular access devices within the scope of the present disclosure may include one or more combinations of the features described herein.

BRIEF DESCRIPTION OF THE SEVERAL VIEWS OF THE DRAWINGS

In order that the above-recited and other features and advantages of the disclosure may be readily understood, a more particular description is provide below with reference to the appended drawings. These drawings depict only exemplary embodiments of vascular access devices according to the present disclosure and are not therefore to be considered to limit the scope of the disclosure.

DETAILED DESCRIPTION OF THE INVENTION

It will be readily understood that the components of the present disclosure, as generally described and illustrated in the figures herein, could be arranged and designed in a wide variety of different configurations. Thus, the following more detailed description, as represented in the figures, is not intended to limit the scope of the disclosure, but is merely a representative of exemplary combinations of the components.

Figure 1:
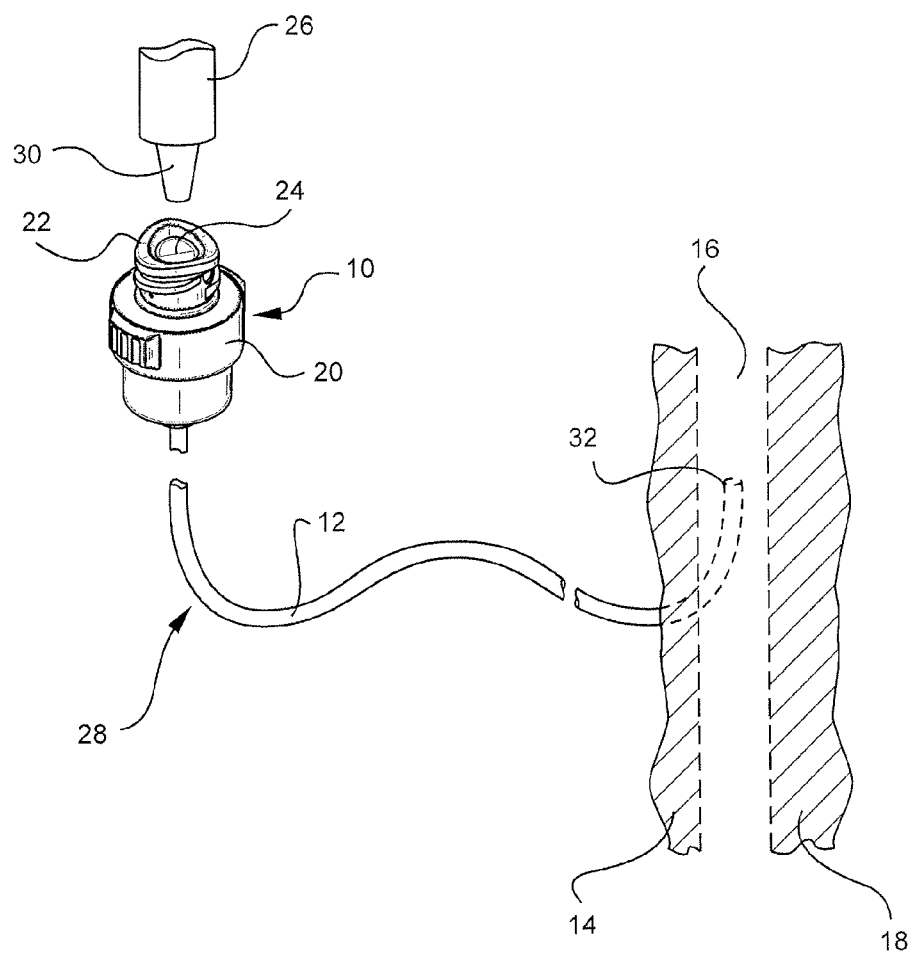
FIG. 1 is a perspective view of an extravascular system connected to the vascular system of a patient.

Referring now to FIG. 1, a vascular access device 10 is used to introduce a substance via a catheter 12 across the skin 14 and into a blood vessel 16 of a patient 18. The vascular access device 10 includes a body 20 with a lumen and a septum 22 placed within the lumen. The vascular access device 10, including the body 20 and the septum 22, will be more thoroughly described with reference to the remaining figures where particular features are better illustrated. As shown in FIG. 1, the septum 22 has a slit 24 through which a separate extravascular device 26, such as a syringe, may introduce a substance into the vascular access device 10. A syringe is one exemplary separate device 26. Other suitable extravascular devices may include additional vascular access devices, IV administration sets, or other common or yet to be developed medical devices.

The device 10 and all structures used in combination therewith may form a larger extravascular system 28. As part of operating the extravascular system 28, a tip 30 of the separate device 26 may be inserted into the vascular access device 10 through the slit 24 of the septum 22. The tip 30 penetrates the device 10 separating at least portions of the two opposing slit surfaces of the septum 22. The septum 22 and the slit 24 may be configured to seal, or at least substantially seal, around the tip 30 as it is inserted into the vascular access device 10. Accordingly, the surfaces near the slit ends may not be separated until the tip 30 is sufficiently inserted into vascular access device 10. The tip 30 serves to open the slit 24 to allow fluid to pass through the device 10, into the catheter 12, and out the end 32 of the catheter when the device is in use.

Figure 2:
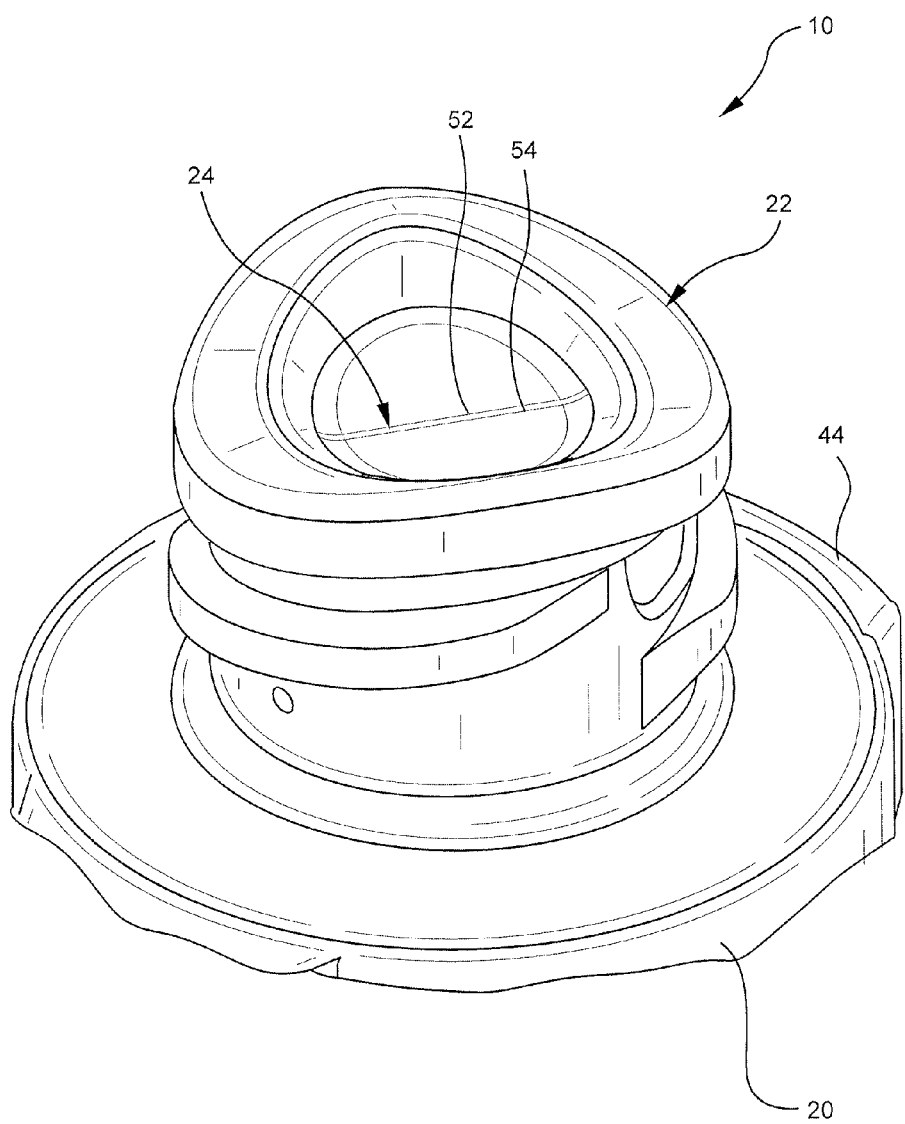
FIG. 2 is a top view of a vascular access device.
Figure 3:
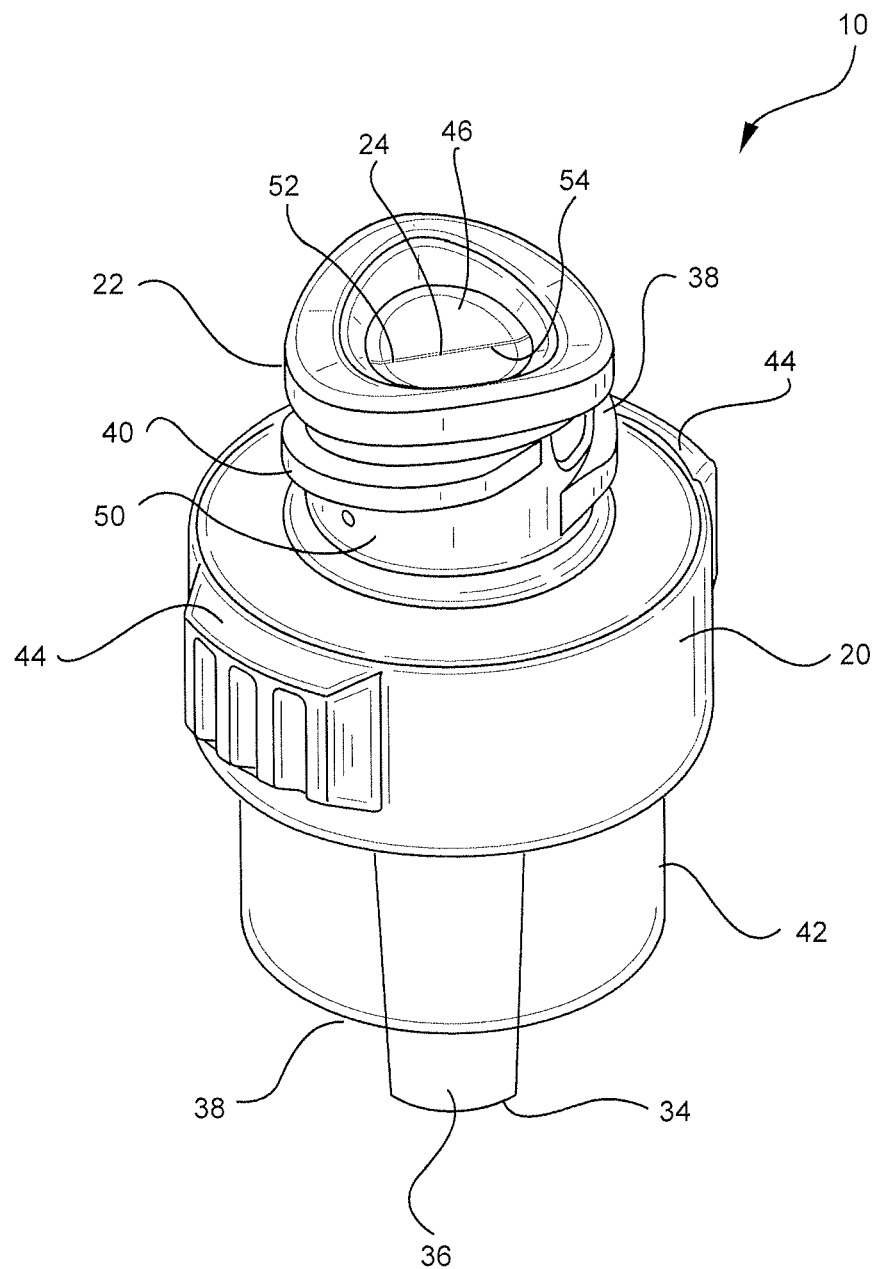
FIG. 3 is a perspective side view of a vascular access device.
Figure 4:
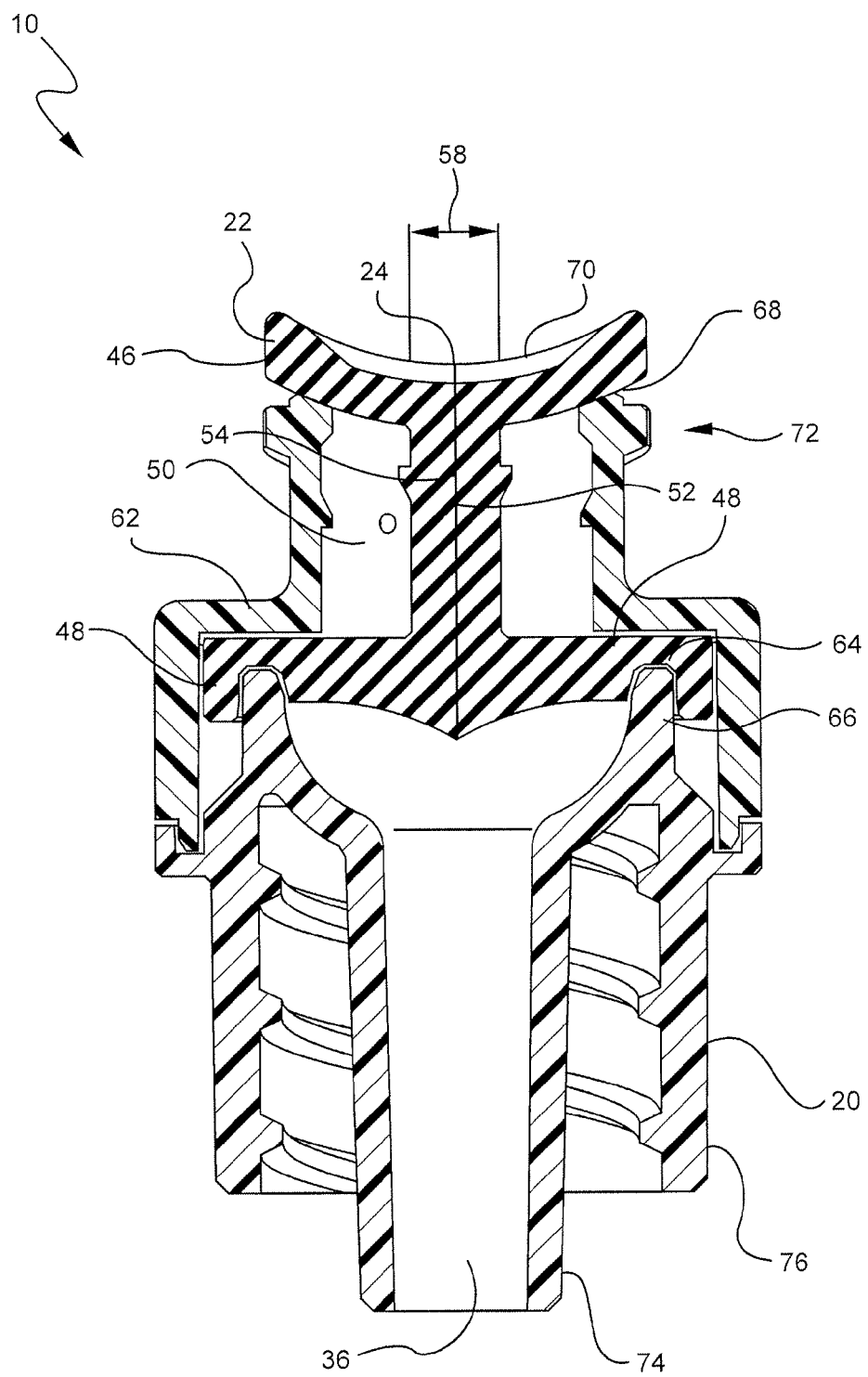
FIG. 4 is a cross section view of a vascular access device.

The features of an example of a vascular access device 10 are illustrated in FIGS. 2, 3, and 4. As illustrated in these figures, the septum 22 includes a portion that extends beyond the body 20 but is otherwise disposed substantially within the body 20. The body 20 may include a cannula 34 for coupling with a catheter or other medical device. The cannula 34, along with other components of the body 20, may cooperate to form a lumen 36 through the body 20. The body 20 may also include connection regions 38, such as female Luer connector 40 or male Luer connector 42, to enable the vascular access device to be selectively coupled to other medical devices.

Additionally, the body 20 may include grips 44, which may be ridges or other structures on the surface of the body 20, to facilitate the manipulation of the vascular access device 10. The body 20 may include other features or structures common to vascular access devices.

With continuing reference to FIGS. 2 and 3, the septum 22 is substantially disposed within the body 20 of the vascular access device 10. More specifically, the septum 22 includes a top disk 46, a bottom disk 48, and a throat region 50 extending between the top disk 46 and the bottom disk 48. The throat section 50 and bottom disk 48 are more clearly visible in the cross section view presented in FIGS. 4 and 5. As used herein, the top disk 46 may also be referred to as a saddle 46 and the bottom disk 48 may be referred to as an anchor 48. With more particular reference to FIG. 2, the septum 22 is shown to include a slit 24 having opposing slit surfaces 52, 54. As described above, the opposing slit surfaces 52, 54 of the slit 24 are moved apart to open the slit when the tip 30 of a medical device is inserted into a vascular access device 10.

Figure 5:
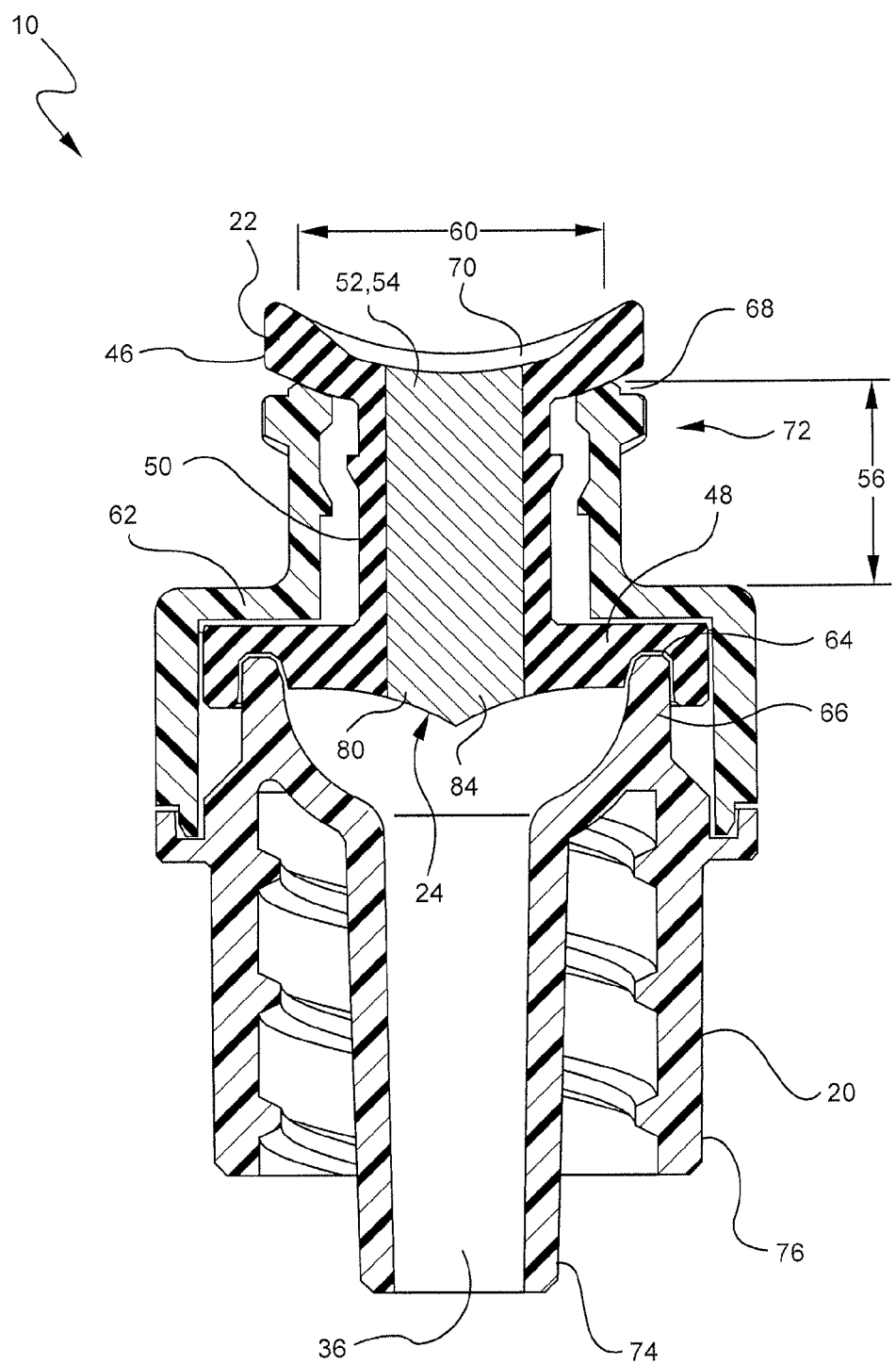
FIG. 5 is a cross section view of a vascular access device with the cross section being 90 degrees offset from the cross section of FIG. 4.

Referring now to FIGS. 4 and 5, cross sectional views of a vascular access device 10 are shown to better illustrate particular aspects of an exemplary septum 22. As illustrated, FIGS. 4 and 5 are cross sections of the same vascular access device with the cross sections being taken along orthogonal lines of cross section. FIG. 4 illustrates a vascular access device 10 showing the throat region 50 spanning between the saddle 46 and the anchor disk 48. The throat region 50 may have any suitable length 56 between the saddle 46 and the anchor 48, which length 56 may vary to accommodate the configuration of the body 20. As one example, the length 56 may be selected to position the anchor disk 48 within the body 20 and the saddle 46 outside the body, as illustrated.

The throat region 50 also has a thickness 58, shown in FIG. 4, and a width 60, shown in FIG. 5. The width 60 and thickness 58 of the throat region 50 may be selected to meet the needs of the medical practitioner and the vascular access device 10 in which the septum 22 is being incorporated. The width 60 may be selected to provide sufficient room for a slit 24 sufficiently wide to accommodate the desired tips 30 of the cooperating medical devices 26. The thickness 58 of the throat region 50 may be selected to provide sufficient strength to the throat region while still providing sufficient elasticity and/or flexibility to allow the slit surfaces 52, 54 to separate as the tips 30 are inserted into the vascular access device 10.

The bottom disk 48, or anchor disk, may be configured to have a size, such as a diameter, that is selected to fit within the body 20 and to be retained in the body by a shoulder region 62. Additionally or alternatively, the bottom disk 48 may be anchored within the body 20 through other means, such as through adhesives or fasteners. As illustrated in FIGS. 4 and 5, the bottom disk 48 may include one or more grooves or slots 64 that may be adapted to cooperate with portions of the body 20 to further anchor the septum 22 in place. The bottom disk 48 and one or more portions of the body 20 may be configured to anchor the septum 22 rotationally within the body, longitudinally within the body, and/or laterally within the body. As one example, fingers 66 of the body 20 may be adapted to fit in the grooves 64 to prevent lateral movement and/or rotational movement of the septum 22. Additionally or alternatively, the fingers 66 may be sized to press the bottom disk 48 into the shoulder region 62 so that the top surface of the bottom disk is in contact with the body 20. As one example, the fingers 66 may cause the bottom disk 48 and the body 20 to form a seal. In addition to the features described, the bottom disk 48 may include additional features or elements customary for vascular access devices.

FIGS. 4 and 5 illustrate that the top disk 46 may be configured to be disposed outside of the body 20. As illustrated the bottom surface of the top disk 46 rests on the upper end 68 of the body 20. FIG. 4 further illustrates that the top disk 46 may be configured to provide a well 70 or indentation. The well 70 may assist in guiding the tip 30 of the cooperating medical device 26 into the slit 24 of the vascular access device 10. As seen in FIGS. 4 and 5, the well 70, in some implementations, may cause the top disk 46 to resemble a saddle. The well 70, when present, may be formed by thinning a portion of the top disk 46 and/or by applying upward pressure to the outside edge of the top disk 46. As one example, the septum 22 may be configured with a throat region 50 that is minimally shorter than the distance between the shoulder region 62 of the body 20 and the upper end 68 of the body. Accordingly, the septum 22 material of the throat region 50 and the top disk 46 may be slightly stretched by this difference causing the top disk to flex forming the well 70. The well 70 may be formed in other suitable manners.

As discussed above and as illustrated in FIG. 4, the top disk 46 contacts the upper end 68 of the body 20. The interface between the top disk 46 and the upper end 68 of the body 20 may form an additional seal, which may be similar to the seal between the bottom disk 48 and the body 20. Additionally or alternatively, an adhesive may be used to bond the top disk 46 to the upper end 68 of the body. Moreover, structural features, such as grooves, may be incorporated into the bottom surface of the top disk 46 to cooperate with the body 20 to form a seal. The seals formed by the top disk 46 and/or the bottom disk 48 and the body 20 are adapted to seal, or at least substantially seal the lumen 36 through the body 20. Moreover, when the slit surfaces 52, 54 are together (i.e., not separated by a tip 30 and not otherwise separated by tears, cracks, or other modifications to the septum 22), the septum 22 seals, or at least substantially seals the passage through the lumen of the body 20.

For purposes of description, the upper end 68 of the body 20 and the portions adjacent thereto may be referred to as a first body end region 72 whereas the lower end 74 of the body 20 and the portions adjacent thereto may be referred to as the second body end region 76. The use of the terms first and second to denominate the end regions, or other elements described herein, is not meant to imply any order between the two end regions but merely to distinguish between the two. While the terms top and bottom are also used herein to designate and distinguish features, components, or parts of the vascular access device, it should be understood that the orientation of the vascular access device may change during use of the device; accordingly, the terms top and bottom are not intended to be limiting with respect to orientation during use of the device but are referencing relative locations in the figure being discussed.

The body 20 and the septum 22 may be constructed of a variety of suitable materials. Commonly, the body 20 of the vascular access device 10 will be made of a plastic, and preferably a plastic material that facilitates molding the body. As illustrated in FIGS. 4 and 5, the body 20 is formed from two pieces that are molded or adhered together to form the body once the septum 22 is in place. Other methods and materials may be used for manufacturing the body 20, some of which may be currently practiced and some of which may be developed in the future.

Similarly, the septum 22 may be made of a variety of suitable materials and through a variety of suitable manufacturing methods. For example, the septum 22 may be formed from liquid silicone rubber through suitable molding procedures, such as insert molding, injection molding, other molding techniques, or a combination of molding techniques. Both the septum 22 and the slit 24 may be formed or prepared using a variety of molding, cutting, drilling, melting, and/or other manufacturing techniques and/or processes described herein.

Figure 6:
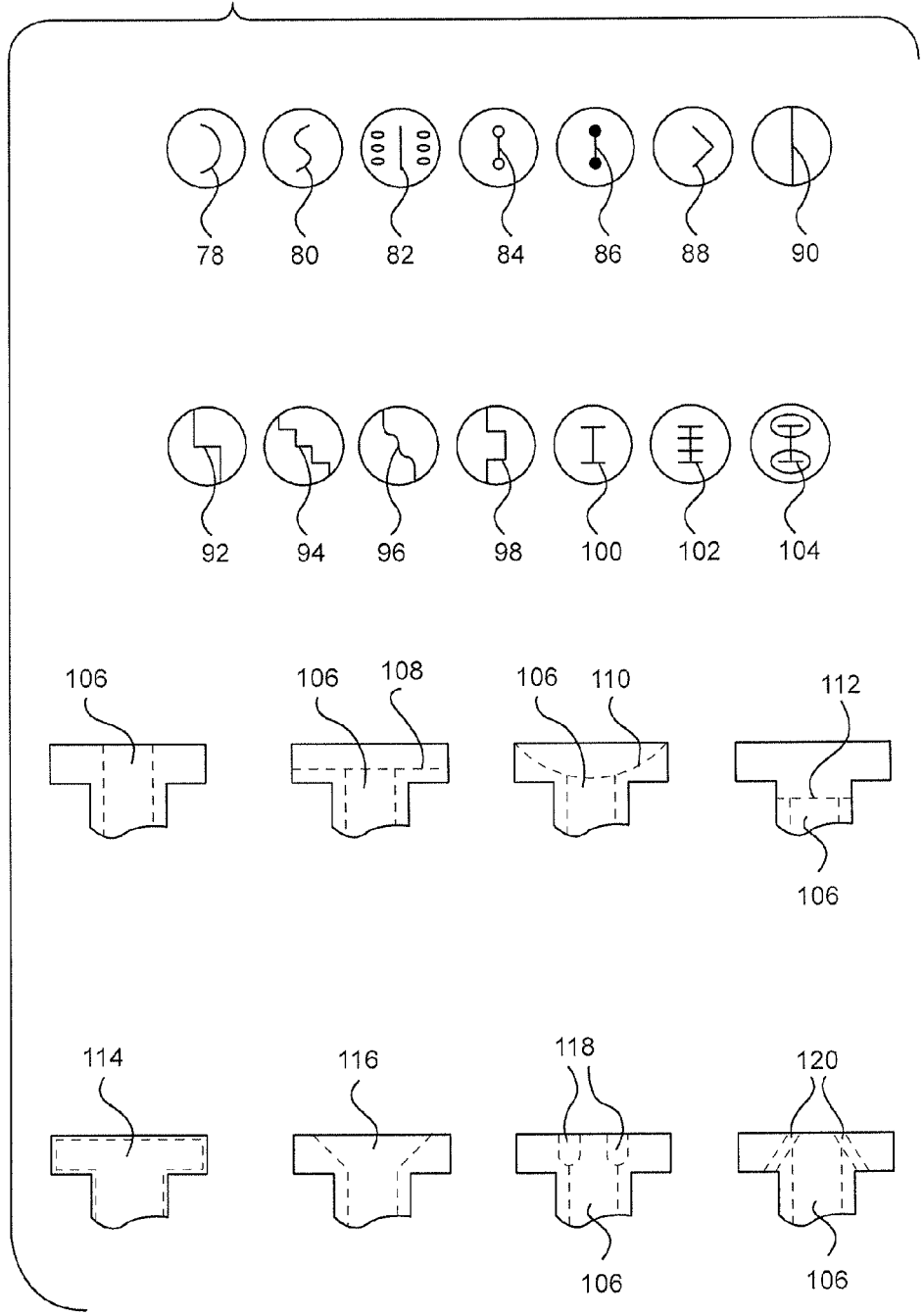
FIG. 6 is a schematic illustration of multiple slit shapes and depths for various septa.

Referring now to FIG. 6, multiple septa 22 are shown in top and side view to illustrate multiple slits which may be formed according to the methods described herein. Slits described herein may include any of the following: an arc-shaped slit 78, a meandering slit such as a sigmoid-shaped slit 80, a slit 82 adjacent one or more structures such as protective structures within the septum 22, a slit 84 with drilled ends, a slit 86 with molded ends, a pointed meandering slit 88, a slit 90 formed across the entire width of the septum 22, a pointed meandering slit 92 extending across the entire width of the septum 22 having two points, a pointed meandering slit 94 extending across the entire width of the septum 22 having more than two points, a sigmoid meandering slit 96 extending across the entire width of the septum 22, a pointed meandering slit 98 extending across the entire width of the septum 22 and returning towards its original path, a slit 100 having multiple intersecting cuts within the septum 22, a slit 102 having additional multiple intersecting cuts within the septum 22, and/or a slit 104 having multiple intersecting cuts in the septum 22 where some of the cuts are surrounded by a material molded within the septum 22. Various other slit formations are possible and are intended to be included within the scope of the claims.

As shown in FIG. 6, various slits, including those described herein, may include various slit depths or angles within the septum 22. For example, any of the following slit depths are possible and may be formed using one or more steps described herein: a straight slit 106, a straight slit 106 combined with a transverse slit 108 of uniform depth, a straight slit 106 combined with a slit 110 of varying depth that increases depth as the slit 110 approaches the axis of the slit 106, a straight slit 106 combined with a deep slit 112 of uniform transverse depth, a slit 114 throughout the entire width and length of the septum 22, a slit 116 with a narrowing taper, a straight slit 106 combined with one or more auxiliary slits 118, and/or a straight slit 106 combined with one or more auxiliary slits and/or slots 120.

Any other varying slit depth and angle may be used as a single slit or combination of slits and will still come within the scope of the claims as supported by examples herein. The slit formations and depths described with reference to FIG. 6 may be formed using any number of conventional or future techniques including cutting, razor cutting, molding, drilling, separating, combining, influencing, bending, tearing, manipulating, and/or any other technique used alone or in combination with any other technique herein. Certain of these techniques are described herein.

Figure 7:
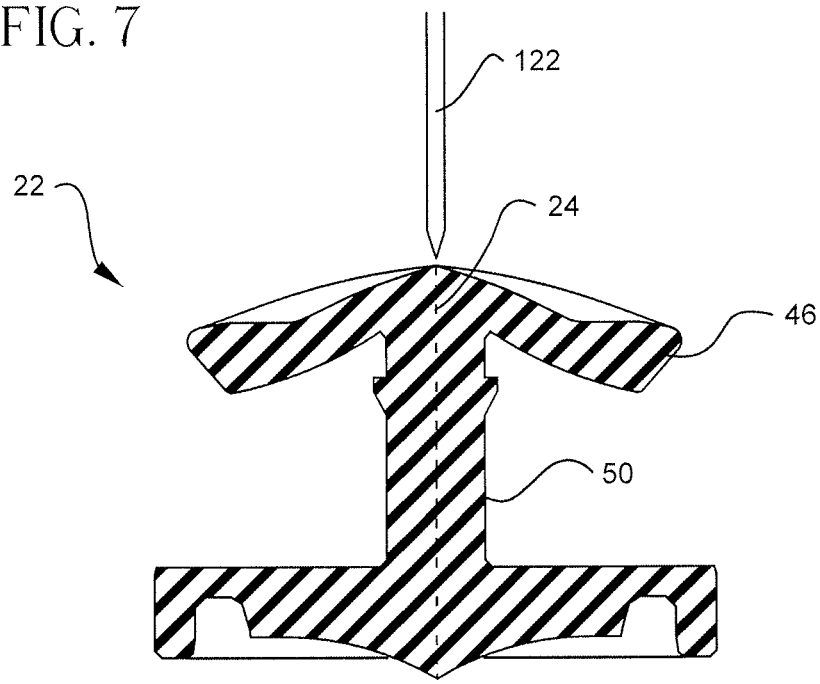
FIG. 7 is a cross section view of a septum illustrating a slit process.

Referring now to FIG. 7, a process of forming a slit 24 within a septum 22 may include cutting the slit and influencing the shape of the septum 22. The process of cutting the septum 22 to form the slit 24 may include, for example, cutting with a blade 122 across a top disk 46 and throat region 50 of the septum 22. During the cutting process, the septum 22 may be supported beneath the top disk 46 and adjacent the throat region 50. The top disk 46 is also influenced to change its shape by flexing the ends of the top disk 46 downward. As the ends of the top disk 46 are flexed downward, the material being cut by the blade 122 along the trajectory of the slit 24 will be less dense. By cutting across less dense material, when the septum 22 returns to its original shape after it is no longer influenced or flexed downward, the slit 24 will be more compact and smaller than it would be otherwise. The process of influencing the shape of the septum 22 in order to provide a less dense cross section along the trajectory of the slit 24 enables the slit 24 to be more resilient when stressed during access by a separate access device 26. Thus, such a slit 24 will open without tearing under stress that would normally cause another slit, i.e., a slit that was not prepared using the shape-influencing technique described with reference to FIG. 7 to tear. The shape of the septum 22 may be influenced by any force in any direction in order to modify the formation of the slit 24. Another example of influencing the shape of the septum 22 is described with reference to FIG. 8.

Figure 8:
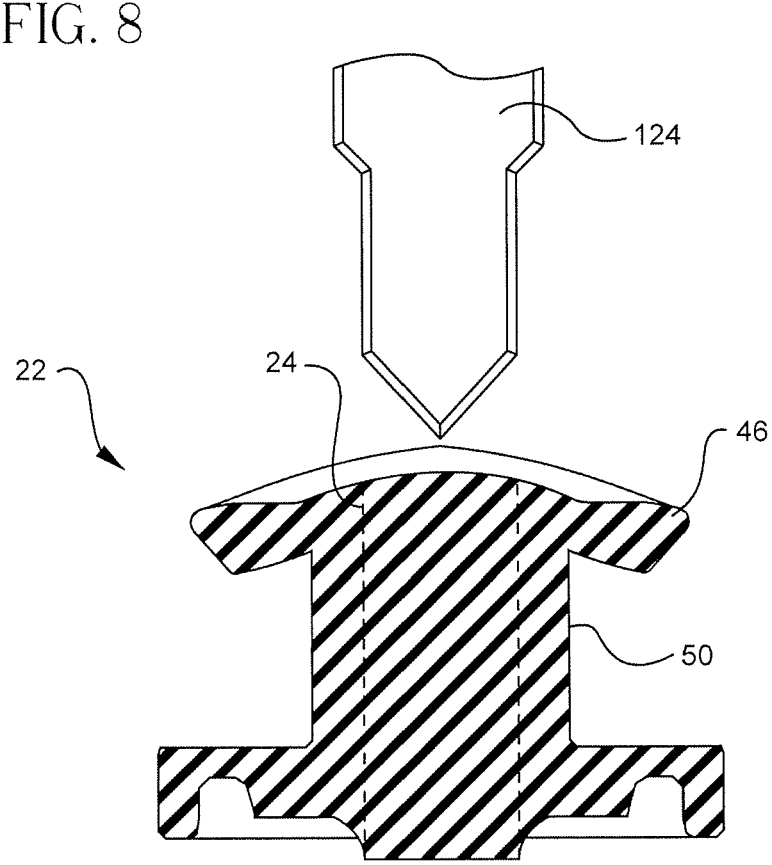
FIG. 8 is a side cross section view of a slitting process of a septum.
Figure 9:
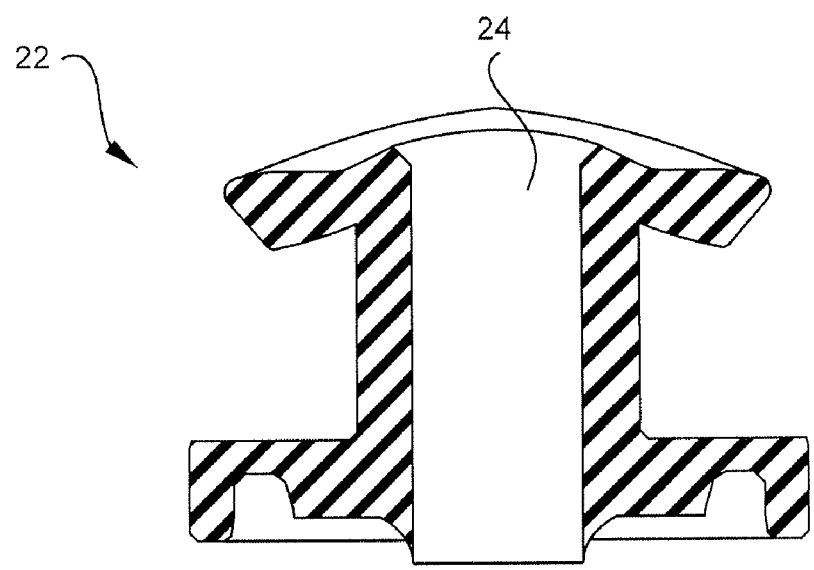
FIG. 9 is a cross section view of an influenced septum.
Figure 10:
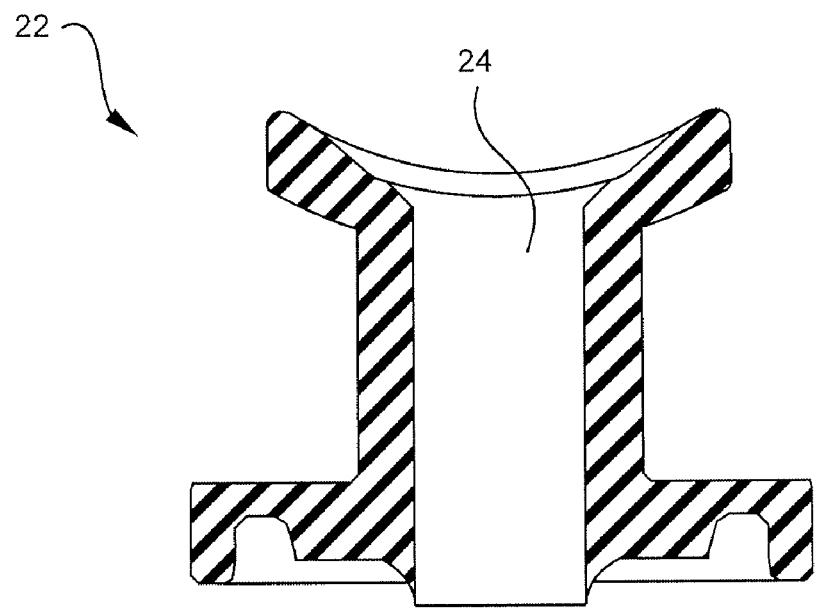
FIG. 10 is a cross section view of a relaxed septum.

Referring now to FIGS. 8-10, a septum 22 may be cut by a V-notch blade 124 to form a slit 24. During the cutting process by the blade 124, the shape of the septum 22 may be influenced. The septum 22 shape is influenced, for example, by supporting the septum 22 underneath its top disk 46 and adjacent its throat region 50 and flexing the ends of the top disk 46 downward and away from the blade 124. Flexing the septum 22 in this direction will provide a wider slit 24, which when relaxed, will become a narrower slit 24 capable of expanding and carrying stress under load of a separate vascular access device 26 without tearing.

Any of the septa 22 illustrated in FIG. 6 may be influenced according to the principles described with reference to FIGS. 7-10 in order to provide the shapes, depths, and angles described for example by the slits illustrated in FIG. 6. For example, the slit 78 may be formed using a straight blade when the top disk of the septum 22 is bent in an arc shape opposite the direction of the arc-shaped slit 78 illustrated in FIG. 6. After a straight cut is made into the top disk of the septum 22, the top disk may be relaxed to allow the straight slit to form an arc shape. Similarly, the slits 80, 88, 92, 94, 96, 98, 110, 116, 118, and/or 120 may be formed during a step of influencing the shape of each respective septum 22. As another example, the slots 120 of the septum 22 described with reference to FIG. 6 may be formed using a single slot procedure after the top disk of the septum 22 is influenced to fold the ends of the top disk upward and towards each other until the slots 120 are in line with each other, forming a single path. A blade, laser, or other mechanism may be used to cut a single path across the folded top disk of the septum 22 to form the separate slots 120 during the same step.

Figure 11:
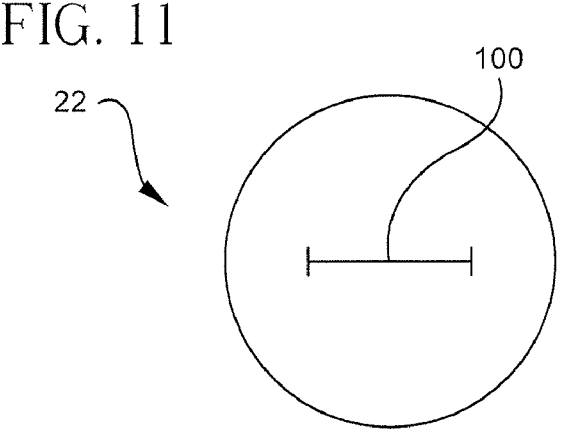
FIG. 11 is a top view of the top disk of a septum having a slit with intersecting portions.
Figure 12:
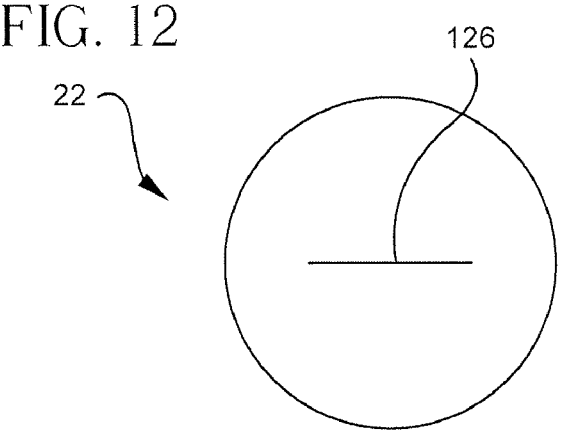
FIG. 12 is a top view of a top disk of the septum of FIG. 11 shown during a step of forming the slit.
Figure 13:
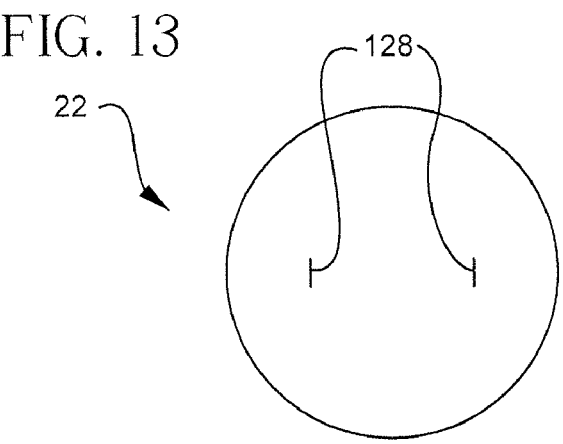
FIG. 13 is a top view of the top disk of the septum of FIGS. 11 and 12 shown during another step of forming the slit.

Referring now to FIG. 11, a septum 22 having a slit 100 with at least one intersecting cut or portion of the slit 100 may be formed by a process involving multiple steps. Any process described herein for forming a slit may include one or more steps. For example, as shown in FIG. 12, the slit 100 illustrated in FIG. 11 may be formed by first cutting a main portion 126 of the slit across the septum 22. Before, after, or during the formation of the main portion 126 of the slit 100, at least one secondary portion 128 may be cut into the septum 22 in order to ultimately intersect with the main portion 126 as shown in FIG. 13. The secondary portions 128 and primary portion 126 then intersect and combine to form the slit 100. As previously described, any depth or angle may be applied to the cuts 126 and 128 forming the slit 100.

Figure 14:
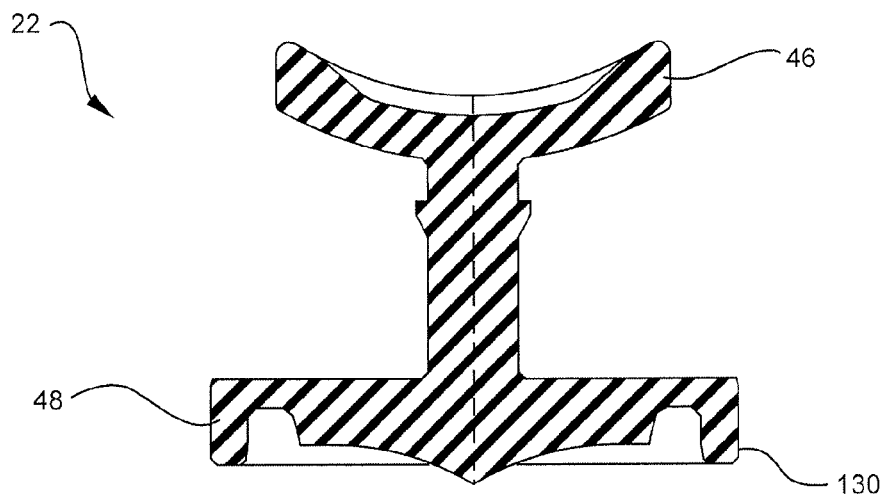
FIG. 14 is a cross section view of a septum showing a traditional molding gate placement.

Referring now to FIG. 14, a cross section view of a septum 22 is shown. Currently, many septa are formed using molding techniques. The gate for infusing material into the mold is identified at location 130. Thus, many gates used during molding techniques of septa 22 include a molding gate located at the bottom disk 48 of the septum 22. Such a location makes it difficult for a manufacturer to control the orientation of a given material's flow and strength at the top disk 46. Since it may be preferable for a manufacturer to control the orientation of the flow of a material within the mold at the top disk 46, a manufacturer may modify the location, number, and direction of molding gates in relation to the top disk 46.

For example, a manufacturer wishing to orient the polymer chains of a material within the top disk 46 in a direction that is perpendicular to the direction of the ends of a slit 24 may place the molding gates at or near the top disk 46.

Figure 15:
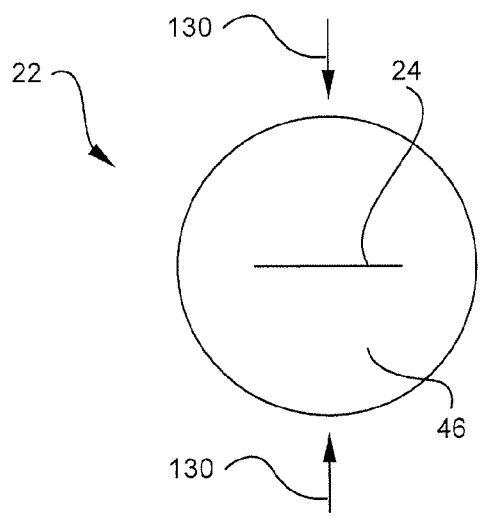
FIG. 15 is a top view of the top disk of a septum showing a modified molding gate placement.
Figure 16:
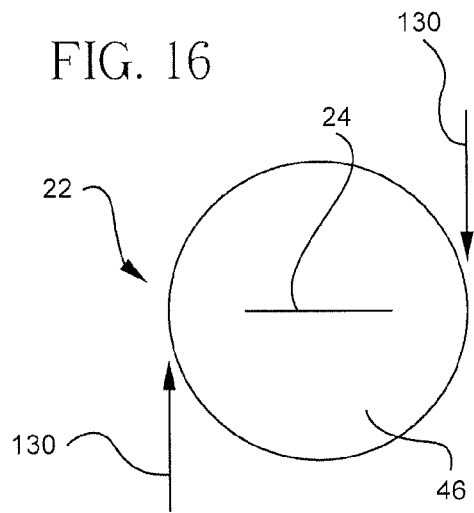
FIG. 16 is a top view of the top disk of a septum showing yet another modified molding gate placement.

Referring now to FIG. 15, a top view of a top disk 46 of a septum 22 is shown with molding gates 130 placed and oriented to encourage the flow of a material in a direction towards a slit 24 and perpendicular to the direction of the ends of the slit 24. Referring now to FIG. 16, the top disk 46 of a septum 22 includes molding gates 130 placed and oriented to encourage a material in a direction that is perpendicular to the direction of the ends of a slit 24. In both FIGS. 15 and 16, the material is likely to flow past the ends of the slit 24 in order to provide a material which, when molded, is less likely to propagate a tear from the ends of the slit 24 in the direction of the ends of the slit 24. The slit 24 may be created prior to or after the use of gates 130. For example, the gates 130 may be used to form the body of the top disk 46. After the top disk 46 is completely molded, the slit 24 may be cut within the top disk 46. As another example, the mold may include a placeholder for the slit 24 and the gates 130 may direct material to flow around the placeholder thus forming the top disk 46. As yet another example, the gates 130 may be used to insert material to be molded around or near the top disk 46 which may already be formed with or without a slit 24.

Any of the septa 22 described herein may include one or more materials formed using multiple techniques, including molding and mechanical attachment. For example, the septa 22 illustrated in FIG. 6 which includes a straight slit 82 may include additional protective materials or structures within the septum 22 to reduce or prevent the risk of septum 22 tearing. Such additional protective structures may be formed of the same or a different material as the material of the septum 22, regardless of the presence of a straight slit. As another example, any elastomeric mesh material may be placed within the top disk 46 of a septum 22 to provide additional support which will discourage or prevent tearing of the septum 22 along the ends of a slit.

The body 20 in communication with any septum 22 described herein may be modified to accommodate the septum 22. For example, the material of the body 20 may be cut, molded, or otherwise formed into a different shape or a structure having different features in order to provide additional support and/or freedom of movement for the septum 22.

It is believed that the disclosure set forth above encompasses multiple distinct inventions with independent utility. While each of these inventions has been disclosed in its preferred form, the specific embodiments thereof as disclosed and illustrated herein are not to be considered in a limiting sense as numerous variations are possible. The subject matter of the inventions includes all novel and non-obvious combinations and subcombinations of the various elements, features, functions and/or properties disclosed herein. Where the disclosure, the presently filed claims, or subsequently filed claims recite "a" or "a first" element or the equivalent thereof, it should be within the scope of the present inventions that such disclosure or claims may be understood to include incorporation of one or more such elements, neither requiring nor excluding two or more such elements.

Applicants submit claims herewith and reserve the right to submit claims directed to certain combinations and subcombinations that are directed to one of the disclosed inventions and are believed to be novel and non-obvious. Inventions embodied in other combinations and subcombinations of features, functions, elements and/or properties may be claimed through amendment of those claims or presentation of new claims in that or a related application. Such amended or new claims, whether they are directed to a different invention or directed to the same invention, whether different, broader, narrower or equal in scope to the original claims, are also regarded as included within the subject matter of the inventions of the present disclosure.

The invention claimed is:

1. A method of manufacturing a vascular access device, comprising:
    providing a body having a first body end region and a second body end region and defining a passage extending through both body end regions;
    preparing a septum, wherein the septum includes a first septum end region and a second septum end region;
    deforming the shape of the septum;
    preparing a slit while the shape of the septum is deformed, the slit extending from the first septum end region to the second septum end region of the septum;
    disposing at least a portion of the septum in the body to at least substantially seal the passage extending through the body, wherein the slit of the septum is adapted to provide selective passage through the septum and the body, and wherein the septum is configured to resist tearing.

2. The method of claim 1,
    wherein the septum has a longitudinal axis;
    wherein the slit has a slit width between a slit first end and a slit second end;
    wherein the slit width extends orthogonally to the longitudinal axis; and
    wherein the septum includes a top disk.

3. The method of claim 1, wherein preparing the slit includes cutting the septum.

4. The method of claim 3, wherein preparing the slit includes cutting multiple intersecting cuts in the septum.

5. The method of claim 1, wherein preparing the slit includes cutting a meandering slit that returns to its original path in the septum.

6. The method of claim 1, wherein preparing the slit includes cutting a curved meandering slit.

7. The method of claim 1, wherein preparing the slit includes cutting a pointed meandering slit having two or more points.

8. The method of claim 1, further comprising molding a protective material in communication with the septum.

9. The method of claim 1, further comprising melting material of the septum after preparing the septum.

10. The method of claim 1, wherein preparing the slit includes combining at least two initially separate portions of the septum.

11. The method of claim 1, wherein preparing the slit includes preparing a slit with varied depths.

12. The method of claim 1, wherein the slit includes at least two ends and wherein preparing the septum includes forming polymer chains in the septum that are oriented at an angle greater than zero degrees in relation to the direction of the ends of the slit.

13. The method of claim 1, wherein the slit includes at least two ends and wherein molding the septum includes forming polymer chains in the septum that are oriented substantially perpendicular to the direction of the ends of the slit.

14. The method of claim 1, wherein the slit includes at least two ends and wherein molding the septum includes directing molding gates in a direction that encourages the flow of a molding material in a direction that is not parallel with the direction of the ends of the slit.

15. A method of manufacturing a vascular access device, comprising:
- providing a body having a first body end region and a second body end region and defining a passage extending through both body end regions;
- forming a septum, wherein the septum includes a first septum end region and a second septum end region;
- cutting a slit in the septum, the slit having a having at least one non-linear portion, the slit extending from the first septum end region to the second septum end region of the septum, the slit being at least one of a slit comprising multiple intersecting cuts, a meandering slit that returns to its original path, a pointed meandering slit with two or more points, and a curved meandering slit;
- disposing at least a portion of the septum in the body to at least substantially seal the passage extending through the body, wherein the slit of the septum is adapted to provide selective passage through the septum and the body, and wherein the septum is configured to resist tearing.

16. The method of claim 15, wherein cutting the slit further includes cutting a slit with varied depths.

17. The method of claim 15, wherein forming the septum includes forming polymer chains in the septum that are oriented at an angle greater than zero degrees in relation to the direction of the ends of the slit.

18. A method of manufacturing a vascular access device, comprising:
- providing a body having a first body end region and a second body end region and defining a passage extending through both body end regions;
- preparing a septum, wherein the septum includes a first septum end region and a second septum end region,
- preparing a slit in the septum, the slit extending from the first septum end region to the second septum end region of the septum, the slit having varied depths;
- disposing at least a portion of the septum in the body to at least substantially seal the passage extending through the body, wherein the slit of the septum is adapted to provide selective passage through the septum and the body, and wherein the septum is configured to resist tearing.

19. The method of claim 18, wherein preparing the slit includes preparing a slit comprising at least one of a slit comprising multiple intersecting cuts, a meandering slit that returns to its original path, a pointed meandering slit with two or more points, and a curved meandering slit.

20. The method of claim 18, wherein preparing the septum includes forming polymer chains in the septum that are oriented at an angle greater than zero degrees in relation to the direction of the ends of the slit.

* * * * *